(12) United States Patent
Snow et al.

(10) Patent No.: US 11,160,540 B2
(45) Date of Patent: Nov. 2, 2021

(54) BIOPSY NEEDLE SAMPLE RETENTION SYSTEM

(71) Applicant: Merit Medical Systems, Inc., South Jordan, UT (US)

(72) Inventors: Jeremy Snow, South Jordan, UT (US); Jacob Forman, West Jordan, UT (US); Darrell Skousen, Lehi, UT (US)

(73) Assignee: Merit Medical Systems, Inc., South Jordan, UT (US)

(*) Notice: Subject to any disclaimer, the term of this patent is extended or adjusted under 35 U.S.C. 154(b) by 421 days.

(21) Appl. No.: 16/142,597

(22) Filed: Sep. 26, 2018

(65) Prior Publication Data
US 2019/0090861 A1 Mar. 28, 2019

Related U.S. Application Data

(60) Provisional application No. 62/564,824, filed on Sep. 28, 2017.

(51) Int. Cl.
*A61B 5/00* (2006.01)
*A61B 10/02* (2006.01)
*A61B 17/3205* (2006.01)
*A61B 17/32* (2006.01)

(52) U.S. Cl.
CPC ...... *A61B 10/0266* (2013.01); *A61B 17/3205* (2013.01); *A61B 2017/32004* (2013.01); *A61B 2017/320064* (2013.01)

(58) Field of Classification Search
CPC ............ A61B 10/0266; A61B 17/3205; A61B 2017/32004; A61B 2017/320064

USPC .................................................. 600/562–567
See application file for complete search history.

(56) References Cited

U.S. PATENT DOCUMENTS

| | | | | |
|---|---|---|---|---|
| 3,831,585 A | * | 8/1974 | Brondy | A61B 17/12099 600/570 |
| 4,781,202 A | * | 11/1988 | Janese | A61B 10/0266 600/567 |
| 4,926,877 A | * | 5/1990 | Bookwalter | A61B 10/0266 600/567 |
| 5,224,488 A | | 7/1993 | Neuffer | |
| 5,462,062 A | * | 10/1995 | Rubinstein | A61B 10/025 600/567 |
| 5,556,563 A | * | 9/1996 | von der Heyde | A61B 17/50 219/227 |
| 5,573,008 A | * | 11/1996 | Robinson | A61B 10/0266 600/567 |

(Continued)

FOREIGN PATENT DOCUMENTS

WO 2016084047 6/2016

OTHER PUBLICATIONS

International Search Report and Written Opinion dated Jan. 16, 2019 for PCT/US2018/052884.
European Search Report dated May 20, 2021 for EP 18862406.8.

*Primary Examiner* — May A Abouelela
(74) *Attorney, Agent, or Firm* — Stoel Rives LLP

(57) ABSTRACT

A biopsy needle assembly configured for use with a tissue biopsy device is disclosed. The biopsy needle assembly may be configured to be advanced to a predetermined tissue sample, sever the tissue sample, and extract the tissue sample from a body tissue of a patient. The biopsy needle assembly may be further configured with two or more cooperating members configured to sever a sample.

11 Claims, 9 Drawing Sheets

(56) References Cited

U.S. PATENT DOCUMENTS

| | | | | |
|---|---|---|---|---|
| 5,595,186 | A * | 1/1997 | Rubinstein | A61B 10/025 600/564 |
| 5,655,542 | A * | 8/1997 | Weilandt | A61B 10/0266 600/567 |
| 5,788,651 | A | 8/1998 | Weilandt | |
| 5,910,121 | A * | 6/1999 | Paolo | A61B 10/025 600/562 |
| 6,022,362 | A * | 2/2000 | Lee | A61B 10/0266 600/564 |
| 6,063,037 | A * | 5/2000 | Mittermeier | A61B 10/025 600/567 |
| 6,080,115 | A * | 6/2000 | Rubinstein | A61B 10/025 600/567 |
| 6,416,484 | B1 * | 7/2002 | Miller | A61B 10/025 600/564 |
| 6,454,727 | B1 * | 9/2002 | Burbank | A61B 10/0233 600/567 |
| 6,540,693 | B2 * | 4/2003 | Burbank | A61B 90/39 600/564 |
| 6,551,254 | B2 * | 4/2003 | Nishtalas | A61B 10/0266 600/567 |
| 6,638,234 | B2 * | 10/2003 | Burbank | A61B 10/0266 600/431 |
| 6,659,105 | B2 * | 12/2003 | Burbank | A61B 10/0266 128/898 |
| 6,997,885 | B2 * | 2/2006 | Lubock | A61B 10/0266 600/564 |
| 7,044,956 | B2 * | 5/2006 | Vetter | A61B 10/0266 606/167 |
| 7,722,550 | B2 * | 5/2010 | McClellan | A61B 10/0266 600/567 |
| 8,137,346 | B2 * | 3/2012 | Burbank | A61B 18/1477 606/49 |
| 8,475,393 | B1 * | 7/2013 | Hameed | A61B 10/0266 600/564 |
| 8,568,334 | B2 * | 10/2013 | Field | A61B 10/0266 600/567 |
| 8,641,640 | B2 * | 2/2014 | Lubock | A61B 10/0275 600/564 |
| 8,771,199 | B2 * | 7/2014 | Theobald | A61B 10/0266 600/562 |
| 9,332,970 | B2 * | 5/2016 | Beck | A61B 10/0233 |
| 9,351,710 | B2 * | 5/2016 | McGhie | A61B 10/0233 |
| 2003/0171694 | A1 | 9/2003 | Casula | |
| 2006/0224082 | A1 * | 10/2006 | Vetter | A61B 90/39 600/564 |
| 2008/0281223 | A1 * | 11/2008 | Goldenberg | A61B 10/0266 600/567 |
| 2008/0281226 | A1 * | 11/2008 | Peters | A61B 10/0275 600/567 |
| 2010/0217208 | A1 * | 8/2010 | Snow | A61M 39/0606 604/246 |
| 2011/0004120 | A1 | 1/2011 | Drubetsky | |
| 2012/0150066 | A1 * | 6/2012 | Goldenberg | A61B 10/0275 600/562 |
| 2014/0207021 | A1 | 7/2014 | Snow | |
| 2015/0065912 | A1 | 3/2015 | Peliks | |
| 2015/0201917 | A1 * | 7/2015 | Snow | A61B 10/0266 600/567 |
| 2016/0045190 | A1 * | 2/2016 | Elfman | A61B 10/0275 600/567 |
| 2016/0081678 | A1 | 3/2016 | Kappel et al. | |

* cited by examiner

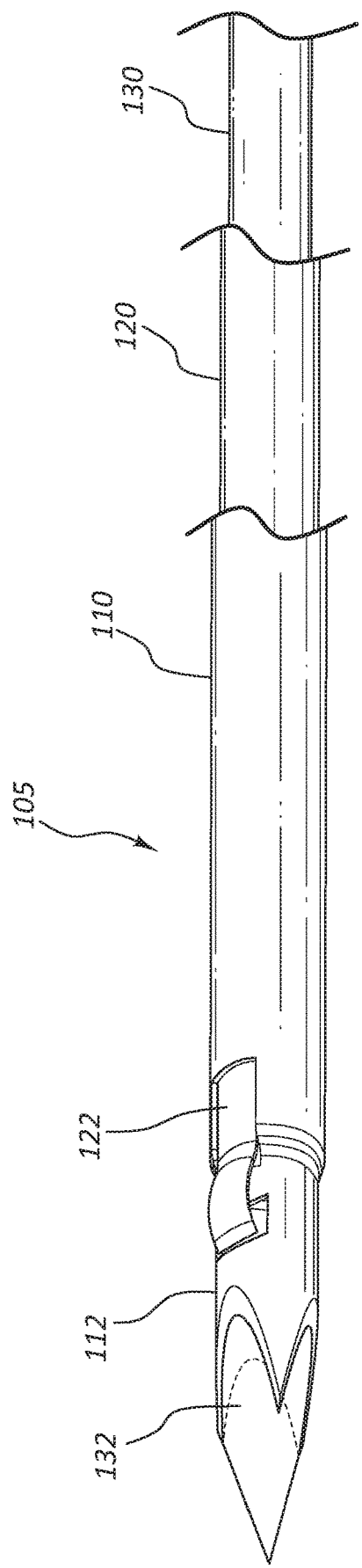
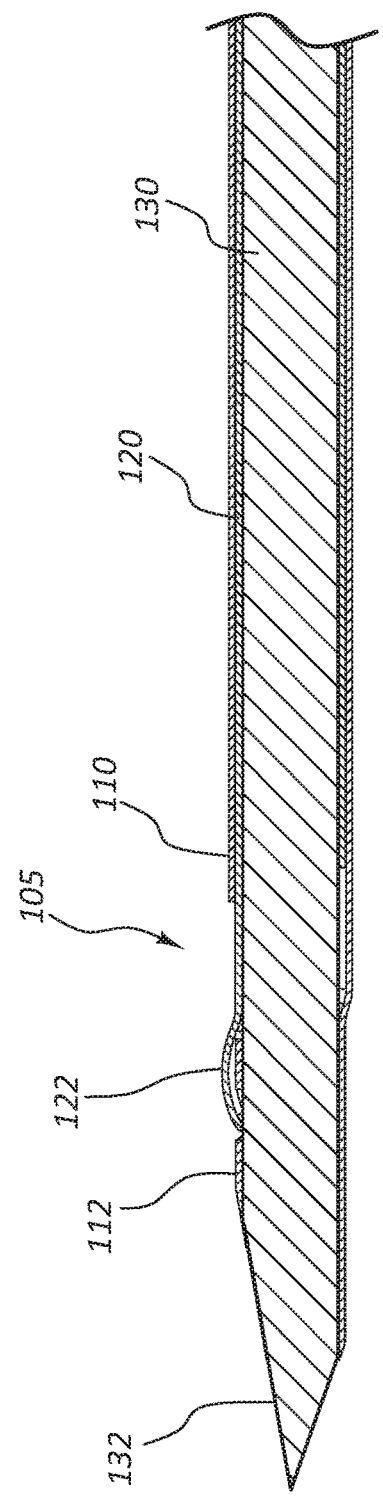
FIG. 2A
FIG. 2B

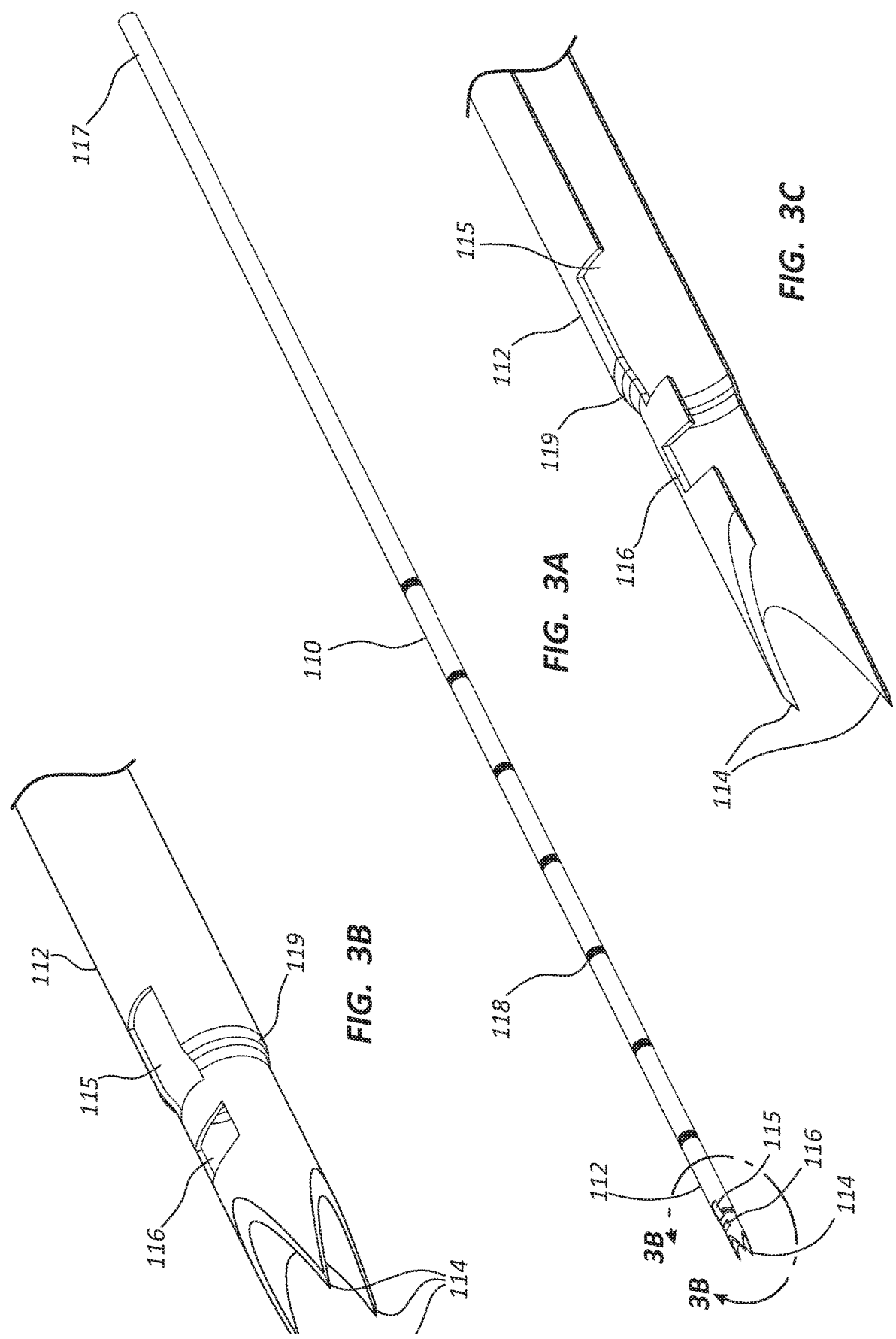

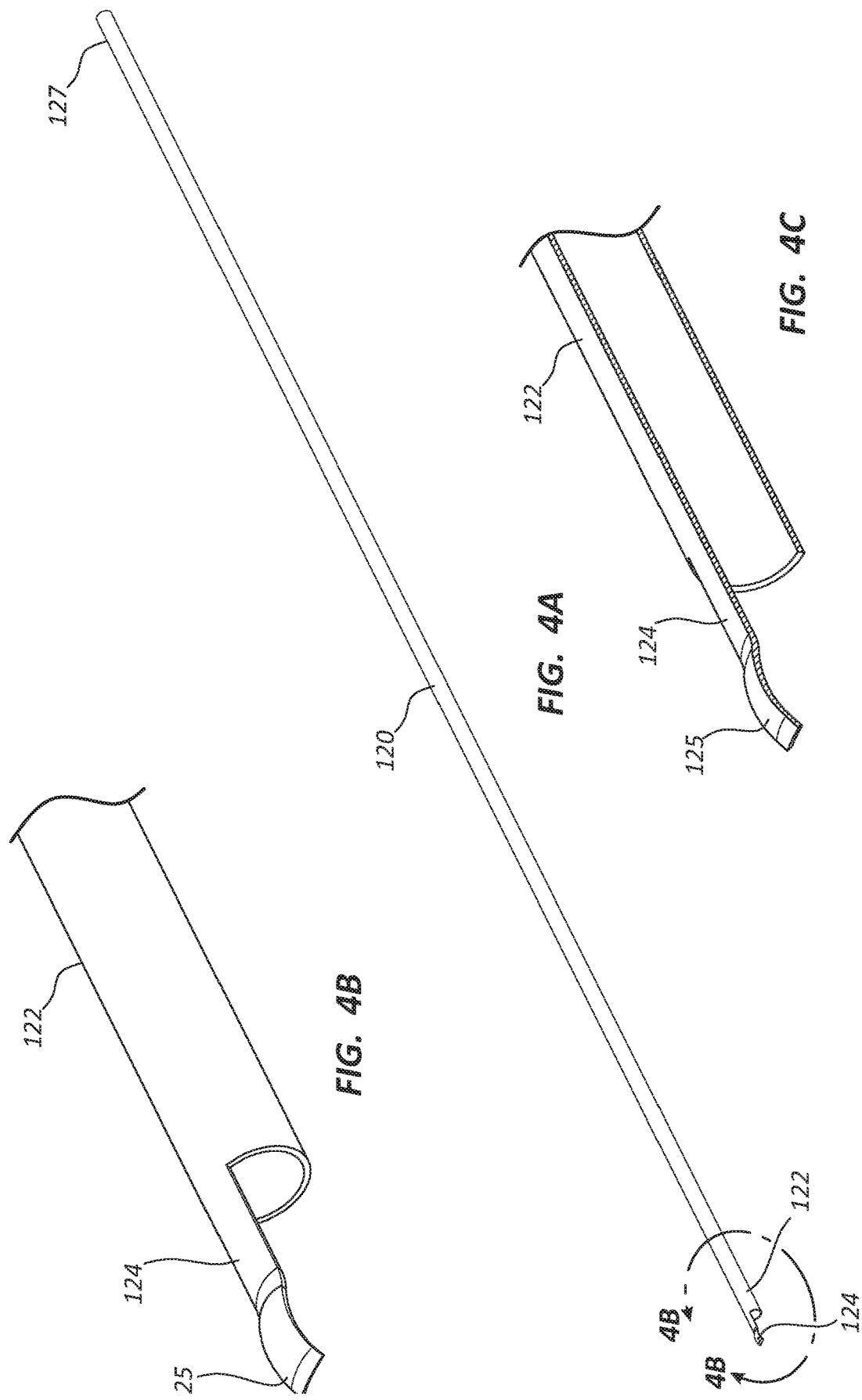

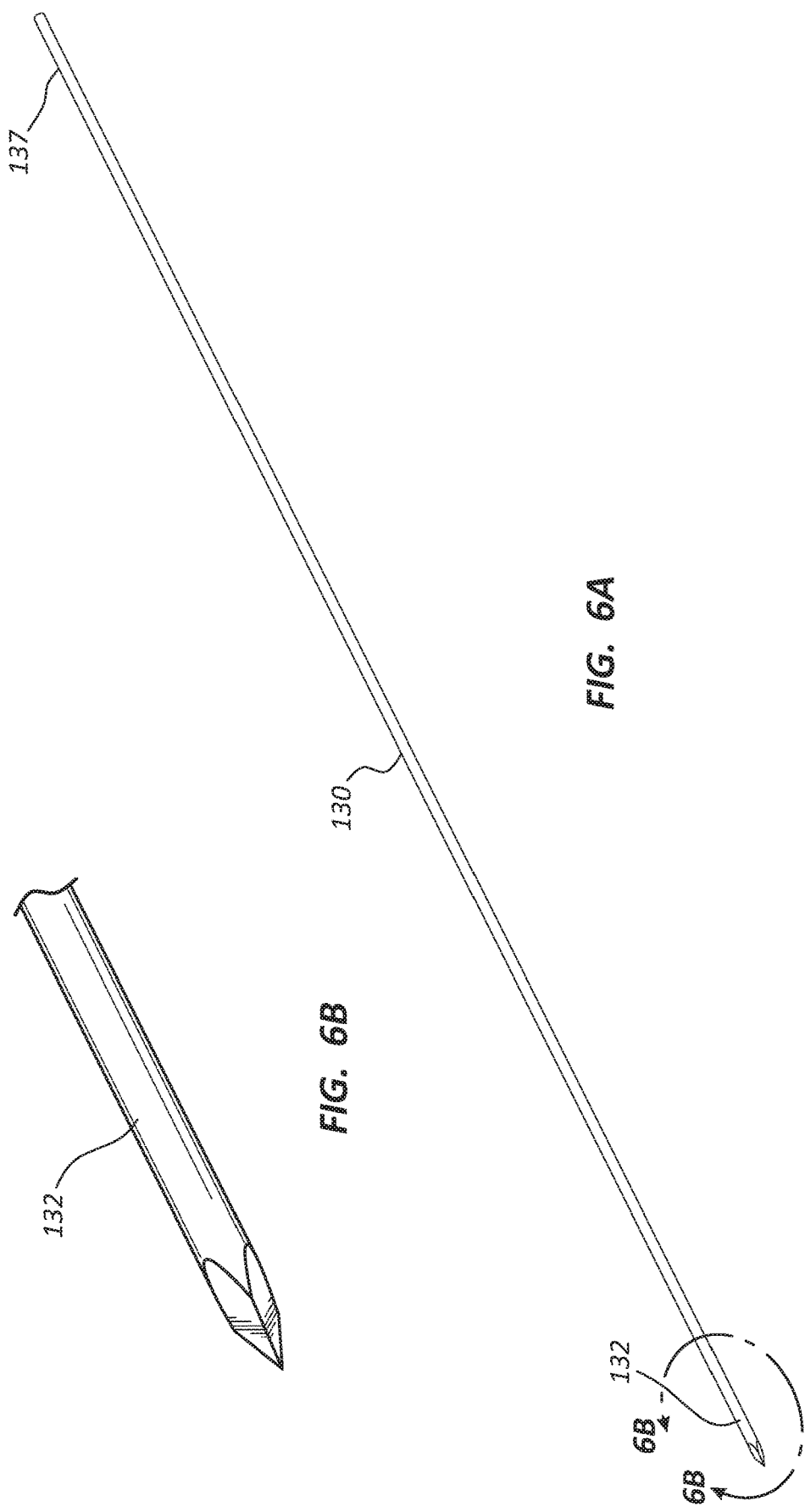

BIOPSY NEEDLE SAMPLE RETENTION SYSTEM

RELATED APPLICATION

This application claims priority to U.S. Provisional Application No. 62/564,824, filed on Sep. 28, 2017 and titled "Biopsy Needle Sample Retention System" which is hereby incorporated by reference in its entirety.

TECHNICAL FIELD

The present disclosure relates generally to medical devices. More specifically, the present disclosure relates to biopsy needle assemblies configured for use with tissue biopsy devices.

BRIEF DESCRIPTION OF THE DRAWINGS

The embodiments disclosed herein will become more fully apparent from the following description and appended claims, taken in conjunction with the accompanying drawings. The drawings depict only typical embodiments, which embodiments will be described with additional specificity and detail in connection with the drawings in which:

FIG. 2A is a perspective view of a portion of a biopsy needle assembly.

FIG. 2B is a cross-sectional view of the portion of the biopsy needle assembly of FIG. 1A.

FIG. 3A is a perspective view of an outer tubular member of the biopsy needle assembly of FIGS. 1A and 1B.

FIG. 3B is a detail view of a distal end portion of the outer tubular member of FIG. 3A taken through line 3B.

FIG. 3C is a detail cross-sectional view of a distal end portion of the outer tubular member of FIG. 3A taken through line 3B.

FIG. 4A is a perspective view of a cutting member of the biopsy needle assembly of FIGS. 2A and 2B.

FIG. 4B is a detail view of a distal end portion of the cutting member of FIG. 4A taken through line 4B.

FIG. 4C is a detail cross-sectional view of a distal end portion of the cutting member of FIG. 4A taken through line 4B.

FIG. 6A is a perspective view of a trocar of the biopsy needle assembly of FIGS. 2A and 2B.

FIG. 6B is a detail view of a distal end portion of the trocar of FIG. 6A taken through line 6B.

DETAILED DESCRIPTION

Figure 1:
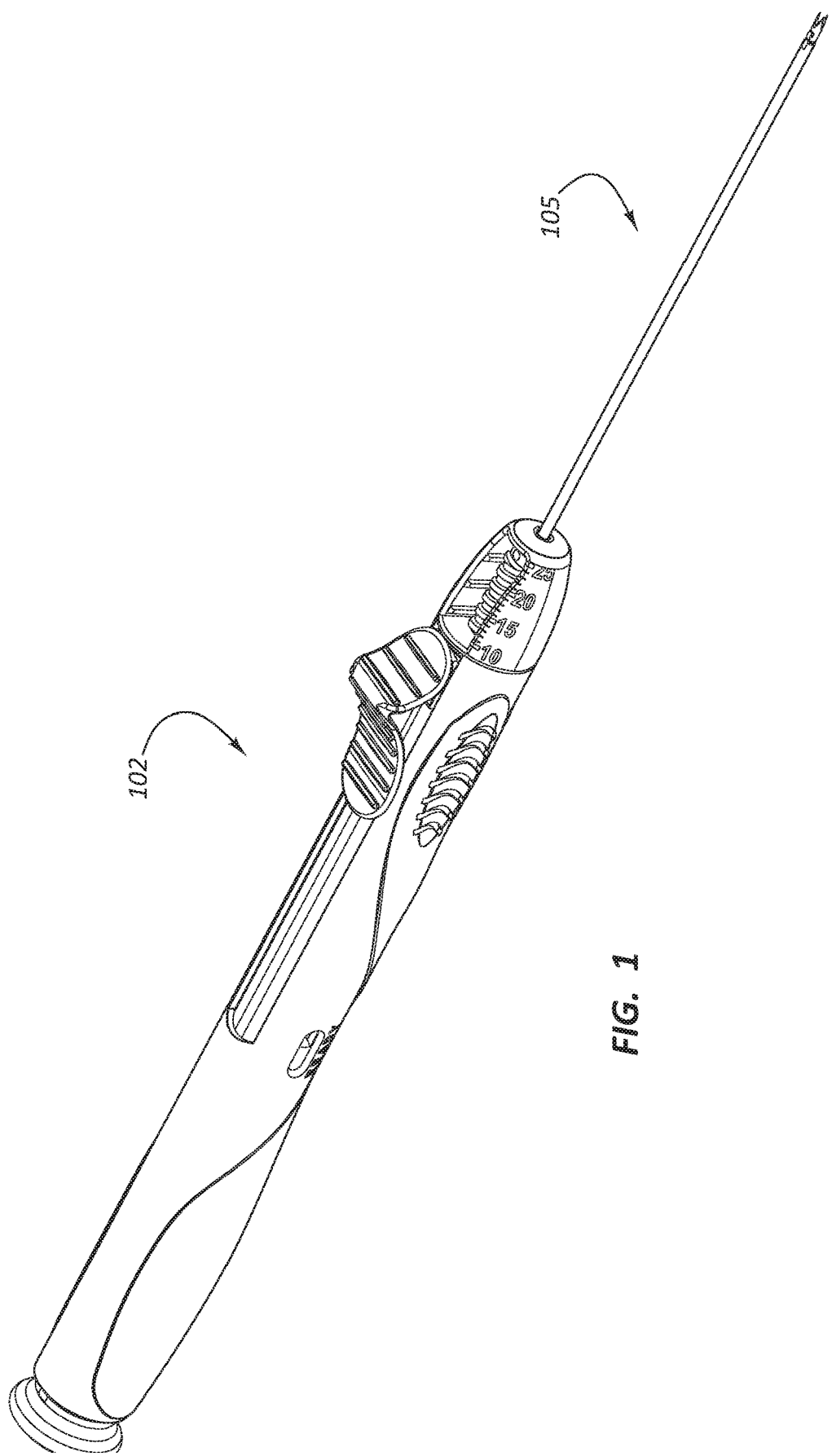
FIG. 1 is a perspective view of a biopsy device.

Tissue biopsy devices may be configured to retrieve tissue samples from various locations within a patient's body. For example, a biopsy device may comprise a biopsy needle assembly, or needle assembly, including tubular members, cutting members, trocars, cannulae, and/or other components configured to access and sever a tissue sample. The needle assembly may be advanced to a location within the body through the skin of the patient (percutaneous access) or may be advanced through a body lumen or other structure. Furthermore, a biopsy device may comprise a handle or actuator configured to displace or deflect at least a portion of the needle assembly such that the needle assembly severs the targeted tissue sample.

Embodiments may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

It will be appreciated that various features are sometimes grouped together in a single embodiment, figure, or description thereof for the purpose of streamlining the disclosure. Many of these features may be used alone and/or in combination with one another.

The phrases "coupled to" and "in communication with" refer to any form of interaction between two or more entities, including mechanical, electrical, magnetic, electromagnetic, fluid, and thermal interaction. Two components may be coupled to or in communication with each other even though they are not in direct contact with each other. For example, two components may be coupled to or in communication with each other through an intermediate component.

The directional terms "distal" and "proximal" are given their ordinary meaning in the art. That is, the distal end of a medical device means the end of the device furthest from the practitioner during use. The proximal end refers to the opposite end, or the end nearest the practitioner during use. As specifically applied to the syringe portion of an inflation device, the proximal end of the syringe refers to the end nearest the handle and the distal end refers to the opposite end, the end nearest the inlet/outlet port of the syringe. Thus, if at one or more points in a procedure a physician changes the orientation of a syringe, as used herein, the term "proximal end" always refers to the handle end of the syringe (even if the distal end is temporarily closer to the physician).

"Tissue" is used in its broadest sense, to refer to any tissue or substance within the human body.

FIGS. 1-8D illustrate different views of a biopsy device and related components. In certain views each biopsy device may be coupled to, or shown with, additional components not included in every view. Further, in some views only selected components are illustrated, to provide detail into the relationship of the components. Some components may be shown in multiple views, but not discussed in connection with every view. Disclosure provided in connection with any figure is relevant and applicable to disclosure provided in connection with any figure or embodiment.

FIG. 1 is a perspective view of a biopsy device 100. The biopsy device 100 is comprised of two sub-assemblies, a handle assembly 102 and a biopsy needle assembly 105. Both sub-assemblies will be described in detail below.

FIG. 2A is a perspective view of a portion of the biopsy needle assembly 105, and FIG. 2B is a cross-sectional view of the portion of the biopsy needle assembly 105 of FIG. 2A. As illustrated, the needle assembly 105 can comprise an outer tubular member 110 comprising a distal end portion 112. In some embodiments, the outer tubular member 110, and/or the distal end portion 112 of the outer tubular member 110, may be configured to cut or sever a first portion of a tissue sample. For example, advancement of the outer tubular member 110 through a tissue sample may core or cut the tissue sample and create a tube-like cut into the tissue, as further discussed below.

Referring to FIG. 2B, the biopsy needle assembly 105 can further comprise a cutting member 120, wherein the cutting member 120 may be at least partially slidably disposed within the outer tubular member 110. As depicted, the cutting member 120 can comprise a distal end portion 122. In certain embodiments, the distal end portion 122 of the cutting member 120 may be configured to displace toward the longitudinal axis of the outer tubular member to cut or sever a distal end portion, or second portion, of the tissue sample. For example, a practitioner, such as a medical doctor, may identify a tissue in a patient to be extracted or sampled from the patient (i.e., for further analysis). The outer tubular member 110 can core or cut into the identified tissue sample and create a tube-like cut into the tissue, thus cutting or severing a first portion of the tissue sample. Subsequently, in some embodiments, the cutting member 120 can be configured to cut or sever a distal end of the tissue sample, or second portion of the tissue sample. Upon severing each of the first and the second portions of the tissue sample, the tissue sample may be separated from surrounding body tissue and the tissue sample may be extracted or removed from the patient, at least in part, by the biopsy needle assembly 105.

Referring again to FIGS. 2A and 2B, the needle assembly 105 can further comprise a trocar 130, wherein the cutting member 120 may be slidably disposed around the trocar 130. The trocar 130 can also comprise a distal end portion 132. In some embodiments, the trocar 130, and/or the distal end portion 132 of the trocar 130, may be configured to facilitate advancement or displacement of the needle assembly 105 through body tissue to a position at or adjacent an identified tissue sample. For example, a practitioner can advance the trocar through the skin and/or tissue of a patient to a position at or adjacent to the site of an identified tissue sample. As the trocar is advanced, the trocar may displace the skin and/or tissue such that a pathway is generated through the skin and/or tissue that may ease advancement of other components of the needle assembly 105 to the position at or adjacent to the site of the tissue sample.

FIG. 3A is a perspective view of the outer tubular member 110 of FIGS. 2A-2B, FIG. 3B is a detail view of the distal end portion 112 of the outer tubular member 110 of FIG. 3A taken through line 3B, and FIG. 3C is a cross-section view of the distal end portion 112 of the outer tubular member 110 of FIG. 3A. The outer tubular member 110 can comprise the distal end portion 112 and a proximal end portion 117. As depicted, the outer tubular member 110 may comprise a lumen 113 along at least a portion of a length of the cutting member 110. The outer tubular member 110 and/or the distal end portion 112 of the outer tubular member 110 may be configured to sever the first portion of the tissue sample. For example, the distal end portion 112 of the outer tubular member 110 may generate or make a tube-shaped cut into or through a body tissue.

The distal end portion 112 of the outer tubular member 110 of FIGS. 3A-3C comprises a plurality of points 114, the points 114 forming a cutting or penetrating edge. The cutting or penetrating edge may be sharp such that the outer tubular member 110, and/or the distal end portion 112 of the outer tubular member 110, is configured to cut or sever at least a portion of the tissue sample. Other cutting arrangements and mechanisms are also contemplated. For example, the distal end portion 112 of the outer tubular member 110 may comprise an annular blade or sharpened edge configured to cut or sever tissue. In the illustrated embodiment, the distal end portion 112 of the outer tubular member 110 comprises three points 114. In other embodiments, the distal end portion 112 of the outer tubular member 110 may comprise one or two points 114, while in yet other embodiments, the distal end portion 112 of the outer tubular member 110 may comprise four, five, six, or more points 114. Distal end portions 112 of outer tubular members 110 comprising any number of points 114 are within the scope of this disclosure.

In some embodiments, at least a portion of the outer tubular member 110, or the distal end portion 112 of the outer tubular member 110, may be configured to allow or permit the outer tubular member 110 to more easily advance or be displaced through the body tissue.

The distal end portion 112 comprises a distal opening 116 and a proximal opening 115. The openings 115, 116 are axially aligned and are spaced from about 0.100 inch to 0.300 inch apart. The spacing is dependent upon the diameter of the outer tubular member 110. For example, if the outer diameter of the outer tubular member is equivalent to a 14 gauge needle then the spacing is approximately 0.263 inch and for a 20 gauge needle the spacing is approximately 0.111 inch. The distal opening 116 may be a rectangular-shape, oval-shape, crescent-shape with the crescent opening directed distally or proximally, square-shape, or any other suitable shape. The distal opening 116 may have an axial length range of from 0.005 inch to 0.100 inch. The width of the distal opening 116 may be equivalent to approximately 65 degrees of the diameter of the outer tubular member 110. The diameter of the outer tubular member may range from 8 gauge (0.165 inch) to 22 gauge (0.028 inch). Therefore, the width of the distal opening 116 may range from approximately 0.059 inch for an 8 gauge outer tubular member 110 to 0.010 inch for a 22 gauge outer tubular member 110.

The proximal opening 115 may be a rectangular-shape with the long side of the proximal opening 115 oriented parallel to the longitudinal axis of the outer tubular member 110. The proximal opening 115 may extend from proximal to a taper 119 to distal of the taper 119 at the distal end portion 112. The width of the proximal opening 115 may be approximately equivalent to the width of the distal opening 116. The openings 115, 116 may be formed in the outer tubular member by any suitable manufacturing technique, such as machining, grinding, laser cutting, electrical discharge machining, etc. The taper 119 may reduce the diameter of the distal end portion 112 aproximately 0.5 gauge. For example, if the outer tubular member is equivalent to an 8 gauge needle at the proximal end portion 117 then the diameter of the distal end portion 112 distal to the taper 119 is approximately equivalent to an 8.5 gauge needle. The taper 119 may be formed utilizing any suitable manufacturing method, such as stretching, swaging, etc.

Also, as illustrated, the outer tubular member 110 can comprise a plurality of indicia 118 configured to indicate to the practitioner a distance that the outer tubular member 110 has advanced into a body tissue (for clarity not all indicia 118 are labeled). For example, each indicium 118 may be positioned 1 cm apart; thus, if the practitioner displaces the outer tubular member 110 into a body tissue up to the third indicia 118 from the distal end portion 112 of the outer tubular member 110, it may indicate to the practitioner that approximately 3 cm of the outer tubular member 110 has been displaced into the body tissue. In some embodiments, the indicia 118 may comprise a plurality of substantially evenly spaced annular lines, marks, or grooves on an outside surface of the outer tubular member 110. In certain embodiments, the indicia 118 may comprise a plurality of tick marks or the indicia may not be evenly spaced. Embodiments of any configuration of indicia are contemplated.

A portion or portions of at least one of the components of the biopsy needle assembly, including, but not limited to, the outer tubular member 110, the indicia 118, the cutting member, and/or the trocar, may also comprise a radiopaque material and/or an echogenic material. A radiopaque material (for example, in combination with a fluoroscope) may aid the practitioner in directing or displacing the needle assembly to a desired or predetermined position within the body tissue of the patient. Bismuth, gold, or other radiopaque materials alone, or in combination, may be used. An echogenic material (for example, in combination with ultrasound) may analogously aid the practitioner in directing or displacing the needle assembly to a desired or predetermined position within the body tissue of the patient. Surface disruptions such as texturing, grooves, dimples, or a combination of materials may also be used.

FIG. 4A is a perspective view of the cutting member 120 of FIG. 1B, FIG. 4B is a detail view of the distal end portion 122 of the cutting member 120 of FIG. 4A taken through line 4B, and FIG. 4C is a cross-section view of the distal end portion 122 of the cutting member 120 of FIG. 4A. As depicted, the cutting member 120 may comprise a lumen along at least a portion of a length of the cutting member 120. The cutting member 120 can further comprise the distal end portion 122 and a proximal end portion 127. In some embodiments, the cutting member 120, and/or the distal end portion 122 of the cutting member 120, may be configured to cut or sever the distal end portion, or second portion, of the tissue sample, as described above. In some other embodiments, at least a portion of the distal end portion 122 of the cutting member 120 may be configured to displace inward toward the central axis of the outer tubular member 110 to cut or sever the distal end portion, or second portion, of the tissue sample. For example, as stated above, the outer tubular member 110 may generate a tube-like cut into the body tissue, severing the first portion of the tissue sample, and the cutting member 120 may be configured to cut or sever the tissue sample at a distal end of the tissue sample, severing the second portion of the tissue sample, at or adjacent a distal end of the tube-like cut made by the outer tubular member 110. For example, the cutting member 120 may be configured to cut or sever the distal end portion, or second portion, of the tissue sample at the same longitudinal position as the distal end of the tube-like cut made by the outer tubular member 110. In other embodiments, the cutting member 120 may be configured to cut or sever the distal end portion, or second portion, of the tissue sample at a position less than 5 mm, less than 4 mm, less than 3 mm, less than 2 mm, or less than 1 mm from the distal end of the tube-like cut made by the outer tubular member 110. In various embodiments, the cutting member 120 may be configured to cut or sever the distal end portion, or second portion, of the tissue sample at a clinically relevant position from the distal end of the tube-like cut made by the outer tubular member 110. The cutting member 120 may also be configured to cut or sever the second portion of the tissue sample at other positions relative to the distal end of the tube-like cut made by the outer tubular member 110.

With continued reference to FIGS. 4A-4C, the cutting member 120 may comprise a finger or tab 124 configured to extend longitudinally from the proximal end portion 122. In some configurations, the tab 124 and the cutting member 120 may be integrally formed from a single piece of material. The cutting member 120 and tab 124 may be formed from any suitable material, such as stainless steel, shape memory metal, etc. In certain embodiments, the tab 124 may comprise a distal portion 125 configured to be disposed into the lumen 113 of the outer tubular member 110 such that the distal portion 125 cuts or severs the second tissue portion. In some embodiments, the end of the distal portion 125 may be squared off, concave, convex, serrated, arrow shaped, barbed, or any other suitable shape to sever or cut the second portion of the tissue sample. The distal portion 125 may be longitudinally curved such that the tab 124 is directed from the outside of the outer tubular member 110 through the distal opening 116 of the outer tubular member 110. The curve may direct the tab 122 through the distal opening 116 at an angle ranging from 5 degrees to 150 degrees dependent upon the length of the distal opening 116. For example, if the distal opening 116 is configured with a long length the angle the tab 124 enters the distal opening 116 may be shallow and if the distal opening 116 has a short length the angle of entrance of the tab 124 into the distal opening 116 may be steep. The curved portion of the tab 124 may be formed by threading the straight tab 124 into the distal opening 116 and then extending the tab 124 against the proximal and distal edges of the distal opening 116 such that the tab 124 curls in a similar manner to curling a ribbon against a scissor blade. Alternatively, the curved portion of the tab 124 may be formed using any suitable technique, such as stamping, rolling, etc. The curved tab 124 may be disposed through the distal opening 116 and into the lumen 113 of the outer tubular member 110 past the central axis of the outer tubular member 110 or at least 50% of the diameter of the lumen 113 of the outer tubular member 110 in order to cut or sever the second portion of the tissue sample.

In some embodiments, the tab 124 may extend through the proximal opening 115 from the lumen 113 of the outer tubular member 110 to the outside of the outer tubular member 110. Prior to activation of the biopsy device 100, the distal end of the tab 124 may be disposed partially into the distal opening 116 such that the distal end does not catch tissue as the biopsy needle assembly 105 is inserted into the patient's tissue. The length of the proximal opening 115 is configured to allow for axial displacement of the cutting member 220 and tab 124 such that the tab 124 passes through the distal opening 116 and past the central axis of the lumen 113 of the outer tubular member 110 to cut or sever the second portion of the tissue sample.

Figure 5A:
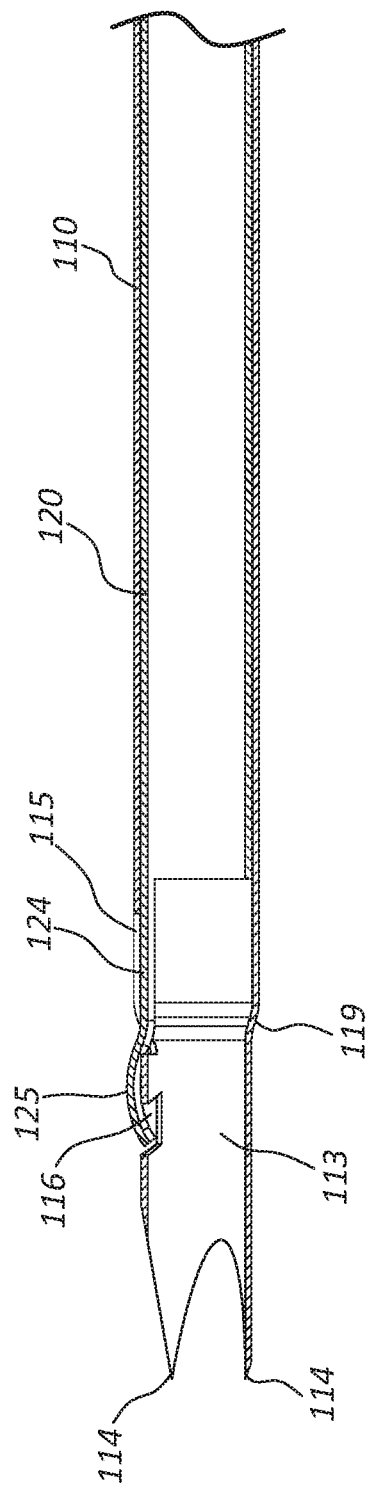
FIG. 5A is a cross-sectional view of portions of the outer tubular member and the cutting member of the biopsy needle assembly of FIGS. 2A and 2B in a first configuration.
Figure 5B:
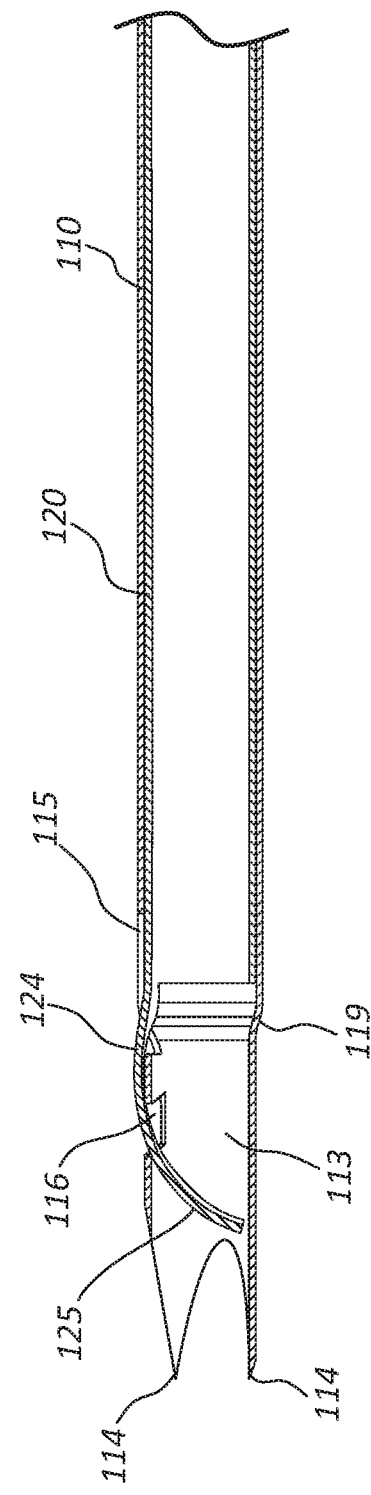
FIG. 5B is a cross-sectional view of the portions of the outer tubular member and the cutting member of the biopsy needle assembly of FIGS. 2A and 2B in a second configuration.

FIGS. 5A and 5B depict cross-sectional views of portions of the outer tubular member 110 and the cutting member 120 of FIGS. 1A and 1B in a first configuration and a second configuration, respectively. FIG. 5A shows a portion of the biopsy needle assembly 105 in the first or ready configuration. At least a portion of the distal end portion 122 of the cutting member 120 is positioned proximal to at least a portion of the distal end portion 112 of the outer tubular member 110. The tab 124 extends distally from a lumen 113 of the outer tubular member 110 and through the proximal opening 115 such that the distal end of the tab 124 is disposed partially within the distal opening 116 such that the distal end of the tab 124 does not catch tissue as the biopsy needle assembly 105 is inserted into the tissue of the patient. FIG. 5B shows a portion of the biopsy needle assembly in a second or activated configuration. The cutting member 120 is translated distally within the outer tubular member 110. A portion of the tab 124 is extending through the distal opening 116 such that the distal end of the tab 124 extends at least to the central axis of the outer tubular member 110. In this configuration, the tab 124 is configured to cut or sever a second portion of a tissue sample.

FIG. 6A is a perspective view of the trocar 130 of FIGS. 2A-2B and FIG. 6B is a detail view of the distal end portion 132 of the trocar 130 of FIG. 6A taken through line 6B. The cutting member 120, as described above, may be slidably disposed around the trocar 130. In some embodiments, the trocar 130 may be fixed with respect to an actuator or handle 102 as described below in connection with FIG. 7. Further, as depicted, the trocar 130 comprises the distal end portion 132 and a proximal end portion 137. The distal end portion 132, as illustrated, can be substantially sharp. In some embodiments, the trocar 130, and/or the distal end portion 132 of the trocar 130, may be configured to facilitate movement of the biopsy needle assembly 105 through body tissue. For example, as described above, a practitioner or user can advance the trocar 130 through the skin and/or tissue of a patient to a position at or adjacent to the site of an identified tissue sample. As the trocar 130 is advanced, the trocar 130 may displace the skin and/or tissue such that a pathway is generated through the skin and/or tissue that may ease advancement of other components of the needle assembly 105 to the position at or adjacent to the site of the tissue sample.

Figure 7:
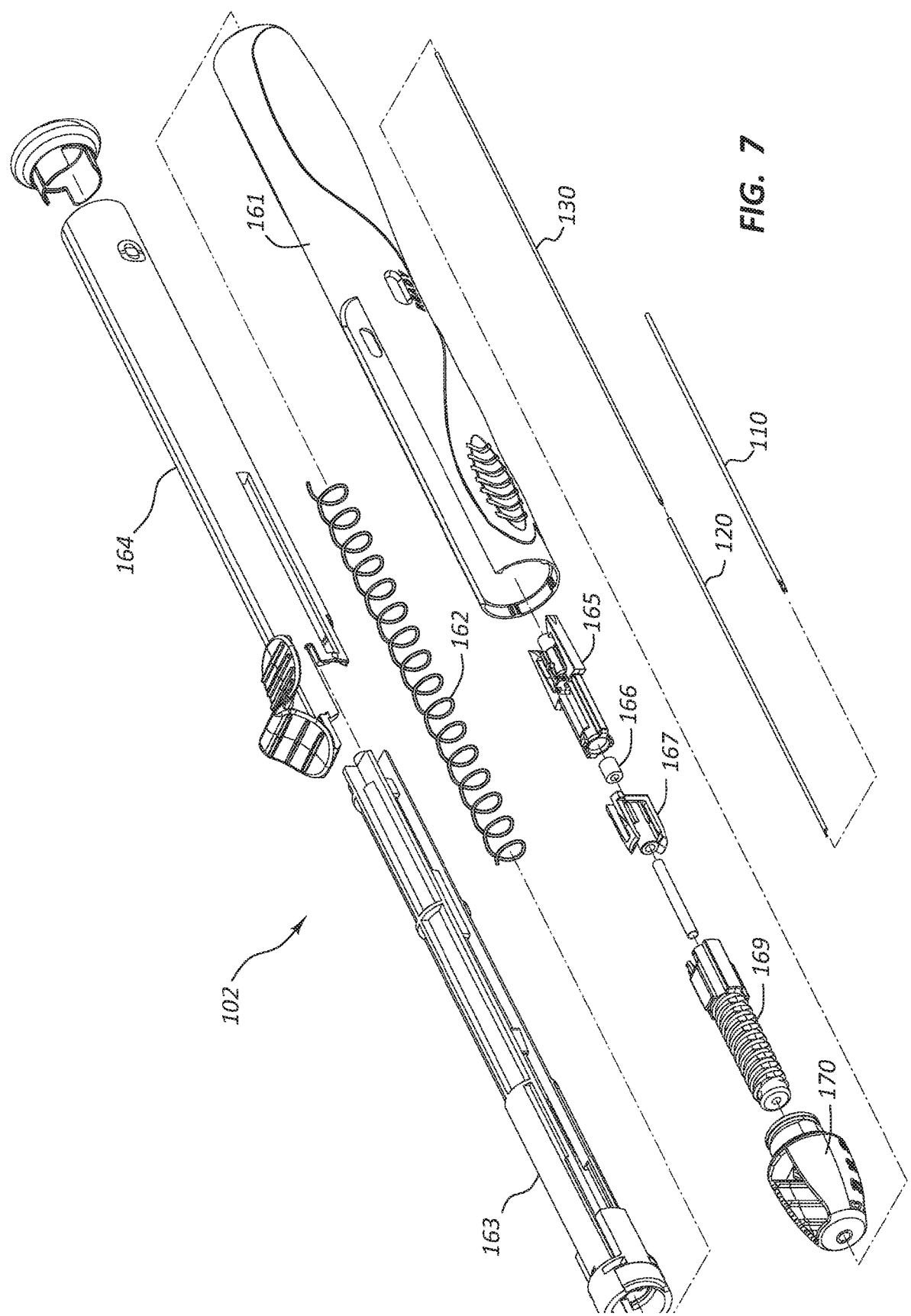
FIG. 7 is an exploded view of a tissue biopsy device of FIG. 1.

FIG. 7 is a perspective exploded view of the tissue biopsy device 100 of FIG. 1. The tissue biopsy device 100 can comprise a needle assembly 105 operatively coupled to a handle 102, or actuator. For example, at least a portion of at least one of the proximal end portions 117, 127, 137 of the outer tubular member 110, the cutting member 120, and/or the trocar 130 may be operatively coupled to the handle 102. The handle 102 may be configured to actuate at least one of the outer tubular member 110, the cutting member 120, and/or the trocar 130 to cut or sever the tissue sample from the body of a patient. In some embodiments, the handle 102 may be configured to actuate at least the outer tubular member 110 and the cutting member 120 to cut or sever the tissue sample from the body. The handle 102 may also be configured to retract the needle assembly 105 from the body and/or to extract the tissue sample from the body of a patient. It is within the scope of this disclosure to couple embodiments of the biopsy needle assembly, as described herein, to any type of handle or actuator. A handle or actuator can have springs and can displace components of the needle assembly 105 relative to each other. A series of steps or displacements of the components of the tissue biopsy device 100 can be effectuated in response to a single input or trigger by a practitioner. Various handles or actuators may be used with the biopsy needle assemblies disclosed herein. For example, U.S. patent application Ser. No. 14/157,935, filed on Jan. 17, 2014 and titled "Impact Biopsy Device and Method of Use," which is hereby incorporated by reference in its entirety, discloses handles and actuators that may be used in connection with the biopsy needle assemblies disclosed here.

FIG. 7 depicts the handle 102 comprising a body member 161, a priming handle 164, a retention tube 163, a spring 162, traveler member 165, a follower member 167, a spacer 166, a threaded portion 169 and a cap 170. The trocar 130 is coupled to the retention tube 163, the outer tubular member 110 is coupled to the follower member 167, and the cutting member 120 is coupled to the traveler member 165. The traveler member 165 is releasably coupled to the follower member 167. The follower member 167 and the traveler member 165 are slidably disposed within the retention tube 163. The traveler member 165 and the follower member 167 are configured to effectuate the sequential linear movement of the cutting member 120 and the outer tubular member 110 as a tissue sample is collected in the biopsy needle assembly.

In some embodiments, in use, the handle 102 is primed for activation when the practitioner pulls the priming handle 164 proximally to compress the spring 162. The biopsy needle assembly 105 is inserted into the tissue of the patient such that the biopsy needle assembly 105 is adjacent to the tissue to be sampled. The handle 102 is activated by the practitioner allowing the spring 162 to decompress. The spring 162 applies an axial force to the traveler member 165 causing the traveler member 165, the follower member 167, the outer tubular member 110, and the cutting member 120 to be disposed distally together while the trocar 130 remains stationary. This movement causes the outer tubular member 110 and the cutting member 120 to enter the target tissue with the first portion of the tissue sample being cut or severed and retained within the distal portion of the lumen 113 of the outer tubular member 110. Linear movement of the follower member 167 and the outer tubular member 110 is stopped when the follower member 167 abuts the proximal end of the threaded portion 169. When the follower member 167 abuts the threaded portion 169 the traveler member 165 is released from engagement to the follower member 167 allowing the traveler member 165 and the cutting member 120 to continue to move distally. Distal movement of the traveler member 165 and the cutting member continues until the traveler member 165 abuts the proximal end of the spacer 166 which is disposed between the traveler member 165 and the follower member 167. The additional movement of the traveler member 165 and the cutting member 120 causes the tab 124 to pass through the distal opening 116 of the outer tubular member 110 and into the lumen 113 of the outer tubular member 110 such that the tissue sample within the outer tubular member 110 is cut or severed by the tab 124. The additional distance the traveler member 165 and the cutting member 120 travel is determined by the length of the spacer 166. The spacer 166 length allows the tab 124 to stop movement within the lumen 113 of the outer tubular member 110 when the distal end of the tab 124 is between the central axis and opposite wall of the outer tubular member 110.

Various tissue biopsy devices utilizing various components, as described above, and/or combinations of said components are also within the scope of this disclosure. For instance, an exemplary tissue biopsy device may comprise a first elongate member configured to be advanced into a body tissue, for example, an elongate member analogous to the trocar 130 of FIGS. 2A and 2B. The tissue biopsy device may further comprise a second elongate member, wherein the second elongate member is disposed around the first elongate member, and wherein the second elongate member is configured to sever a first portion of a tissue sample, for example, an elongate member analogous to the outer tubular member 110 of FIGS. 2A and 2B. Additionally, the tissue biopsy device may comprise a third elongate member, wherein the third elongate member may be movably disposed within the second elongate member and around the first elongate member, and wherein the third elongate member is configured to sever a second portion of the tissue sample at or adjacent a distal-most point of a distal end portion of the second elongate member, for example, an elongate member analogous to the cutting member 120 of FIG. 2B. In some embodiments, the third elongate member may be configured to cut or sever the second portion of the tissue sample at the same longitudinal position as the distal-most point of the distal end portion of the second elongate member. In other embodiments the third elongate member may be configured to cut or sever the second portion of the tissue sample at an optimized position from the distal-most point of the distal end portion of the second elongate member. The third elongate member may also be configured to cut or sever the second portion of the tissue sample at other positions relative to the distal-most point of the distal end portion of the second elongate member. The third elongate member may also be configured to retain the second portion of the tissue sample within the needle assembly 105 when the needle assembly 105 is withdrawn from the tissue of the patient. Further, the tissue biopsy device may comprise an actuator, for example, an actuator analogous to the handle 102 of FIG. 1. The actuator may be configured to displace or deflect at least one of the second elongate member and the third elongate member such that the tissue sample is severed. The actuator may also be configured to retract each of the first elongate member, the second elongate member, the third elongate member, and/or the tissue sample from the body of a patient.

FIGS. 8A-8D are schematic in nature. In other words, the figures show the functional and operational relationships of a portion of the biopsy needle assembly 105 upon use in a patient, but the figures are not intended to indicate any particular structure or spatial disposition of any tissue, organ, body component, or group of body components in the patient. Additionally, the schematic representations herein may be drawn to show internal tissues and/or organs of the patient without explicitly designating cross-sections or cutaways of the tissues and/or organs. For example, a body tissue may be schematically shown with the biopsy needle assembly disposed therein without indicating a cross-section portion or cutaway of a portion of the body tissue. FIGS. 8A-8D are schematic representations of cross-sectional views of the portion of the needle assembly 105 of FIGS. 2A-2B in a first configuration, a second configuration, a third configuration, and a fourth configuration respectively.

Figure 8A:
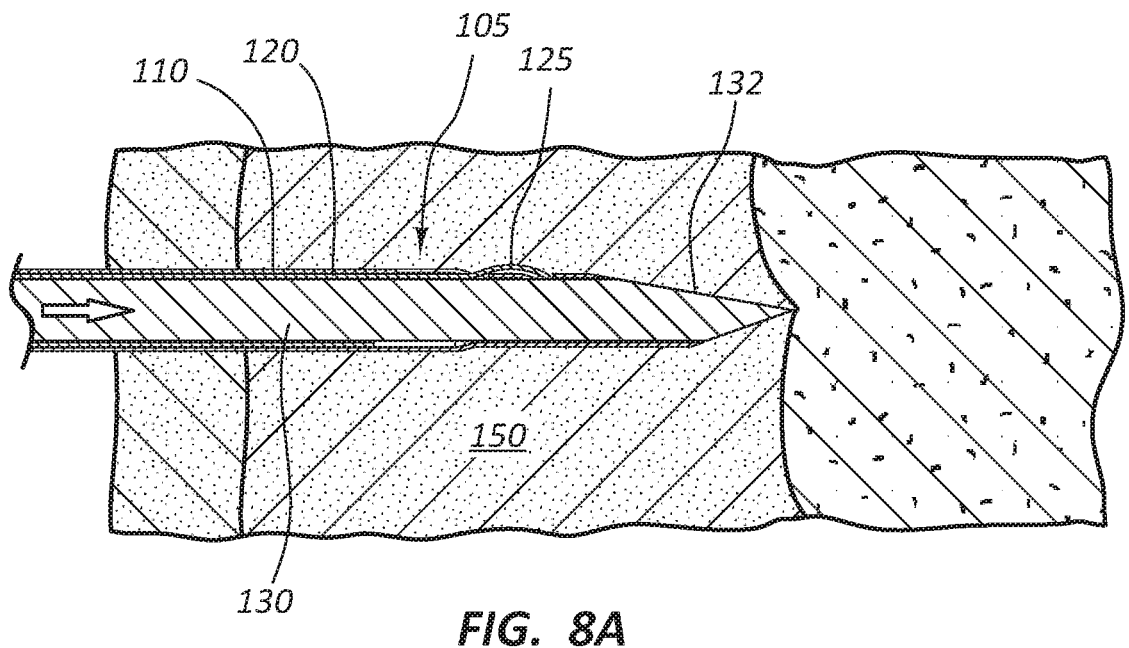
FIG. 8A is a schematic cross-sectional representation of portions of the outer tubular member, the cutting member, and the trocar of the biopsy needle assembly of FIGS. 1A and 1B in a first configuration.

FIG. 8A illustrates the outer tubular member 110, the cutting member 120, and the trocar 130 of the needle assembly 105 advanced into a body tissue 150, as shown by the arrow, in the first configuration. In some embodiments, a practitioner may determine a tissue sample to obtain. As such, the distal end portion 132 of the trocar 130 may be disposed to a position at or adjacent a proximal end portion of the predetermined tissue sample. In the first configuration, the sharp end of the trocar extends distally beyond the distal end portion 112 of the outer tubular member 110 and the distal end portion 122 of the cutting member 120 such that the trocar may cut a path through the patient's tissue. The distal end of the tab 124 is at least partially disposed within the distal opening 116 of the outer tubular member 110 such that the distal end does not catch tissue as the needle assembly 105 is inserted into the patient's tissue.

Figure 8B:
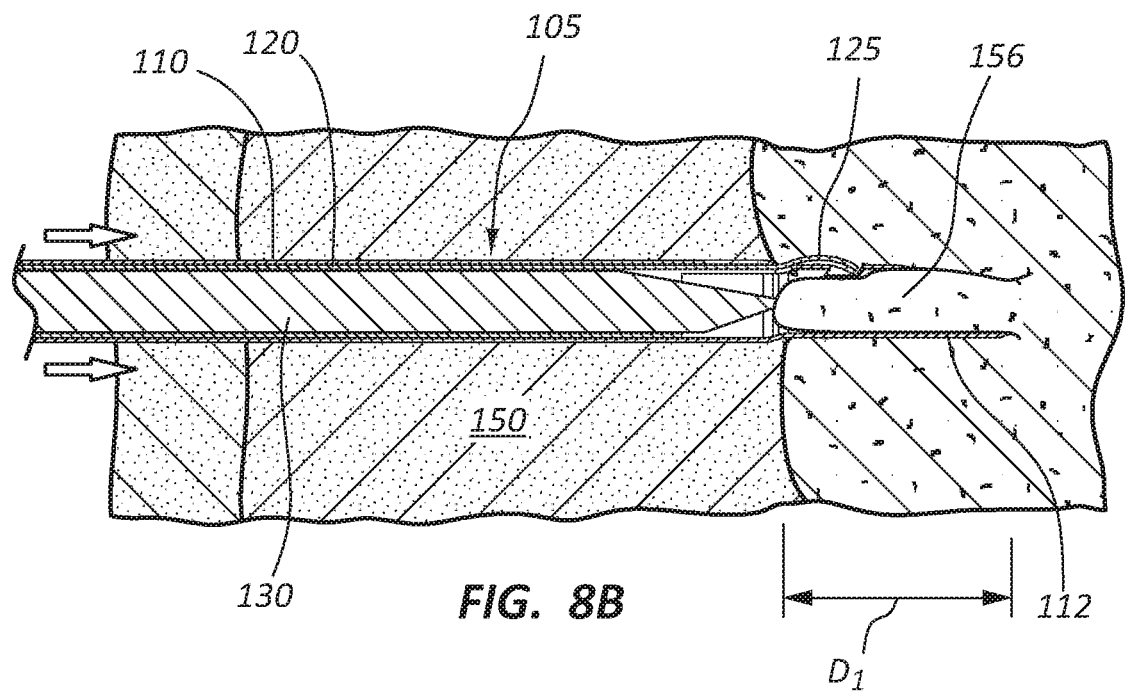
FIG. 8B is a schematic cross-sectional representation of the portions of the outer tubular member, the cutting member, and the trocar of the biopsy needle assembly of FIGS. 1A and 1B in a second configuration.

FIG. 8B illustrates the outer tubular member 110, the cutting member 120, and the trocar 130 of the needle assembly 105 advanced into a body tissue 150, as shown by the arrow, in the second configuration. The outer tubular member 110 and the cutting member 120 are displaced distally into the tissue to be sampled. As depicted, such displacement of the outer tubular member 110 can sever a first portion of a tissue sample 156. In some embodiments, the outer tubular member 110 can be displaced distally relative to the trocar 130, such that the distal end portion 112 of the outer tubular member 110 is extended a distance, or stroke length, into the body tissue 150 relative to the trocar 130. The length $D_1$, as identified in FIG. 8B, represents the stroke length, as described above.

Figure 8C:
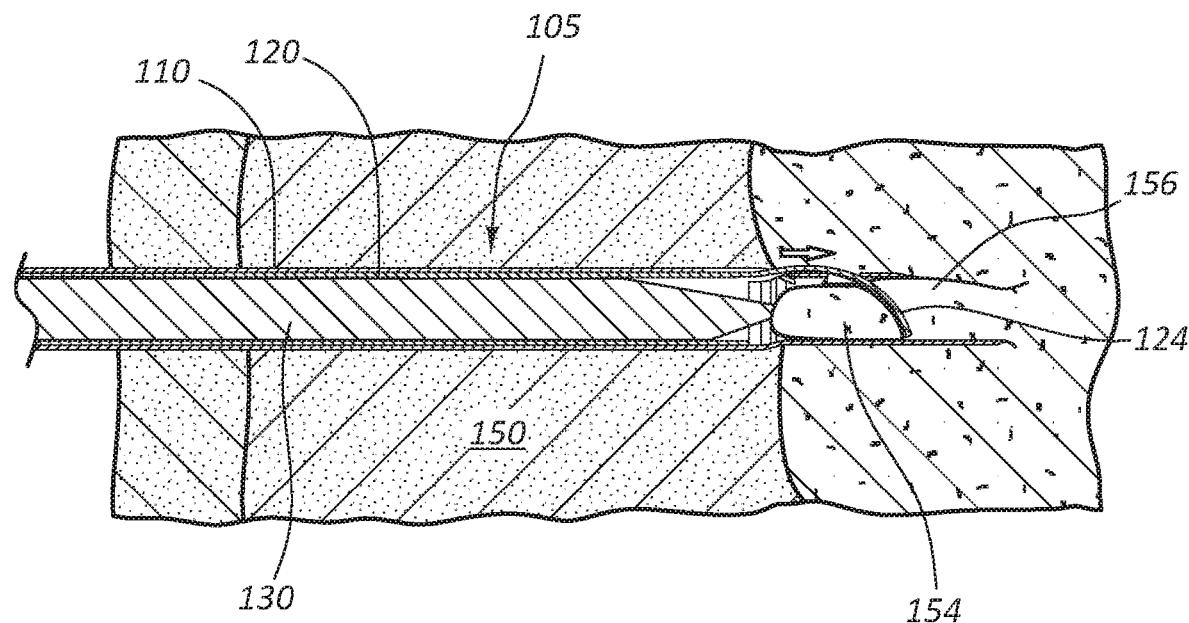
FIG. 8C is a schematic cross-sectional representation of the portions of the outer tubular member, the cutting member, and the trocar of the biopsy needle assembly of FIGS. 1A and 1B in a third configuration.

FIG. 8C illustrates the outer tubular member 110, the cutting member 120, and the trocar 130 of the needle assembly 105 advanced into a body tissue 150, as shown by the arrow, in the third configuration. The cutting member 120 is displaced distally relative to the outer tubular member 110. Displacement of the cutting member 120 may result in at least the distal end of the tab 124 severing a second portion 154 of the tissue sample 156 at or adjacent a distal-most point of the distal end portion 112 of the outer tubular member 110. For example, the cutting member 120 may be configured to cut or sever the second portion 154 of the tissue sample 156 at the optimized position from the distal-most point of the distal end portion 112 of the outer tubular member 110. The cutting member 120 may also be configured to cut or sever the second portion 154 of the tissue sample 156 at the same longitudinal position as the distal-most point of the distal end portion 112 of the outer tubular member 110. The cutting member 120 may also be configured to cut or sever the second portion 154 of the tissue sample 156 at other positions relative to the distal-most point of the distal end portion 112 of the outer tubular member 110.

In some embodiments of the present disclosure, the configuration of the distal end portion 122 of the cutting member 120 with respect to the distal end portion 112 of the outer tubular member 110 may be such that the distal end of the tissue sample 154 is severed at or adjacent the distal end portion 112 of the outer tubular member 110. In certain configurations, the distal end portion 122 of the cutting member 120 can pass through the distal opening 116 of the outer tubular member 110 such that the distal end portion 122 of the cutting member 120 is configured to sever the second portion 154 of the tissue sample 156. As described above, severing the second portion 154 of the tissue sample 156 may comprise displacing at least a portion of the distal end portion 122 of the cutting member 120 toward a central axis of the cutting member 120.

In some embodiments, actuation of the outer tubular member 110 and/or the cutting member 120 may be effectuated by a handle or actuator, such as handle 102 of FIG. 6. In certain embodiments, displacement of the outer tubular member 110 may occur prior to the displacement of the cutting member 120. In certain other embodiments, displacement of the outer tubular member 110 and the cutting member 120 may occur substantially simultaneously. The position of the trocar may remain substantially stationary during the displacement of each of the outer tubular member 110 and the cutting member 120. Other timing and/or sequences of the displacement of each of the outer tubular member 110 and the cutting member 120 are also contemplated.

Upon severing of the tissue sample 154, as illustrated in FIG. 8C, each of the trocar, the outer tubular member 110, the cutting member 120, and the trocar 130 may be retracted from the body tissue 150 of the patient with the tissue sample 154 retained within the lumen 113 of the outer tubular member 110 by the tab 124. In certain embodiments, relative positions of each of the trocar 130, the outer tubular member 110, and the cutting member 120 may be substantially maintained upon the retraction of the each of the trocar 130, the outer tubular member 110, and the cutting member 120 from the body tissue 150. The tab 124 of the cutting member may act as a barrier to retain the tissue sample 154 within the lumen 113 of the outer tubular member 110 during retraction of the biopsy needle assembly 105.

Figure 8D:
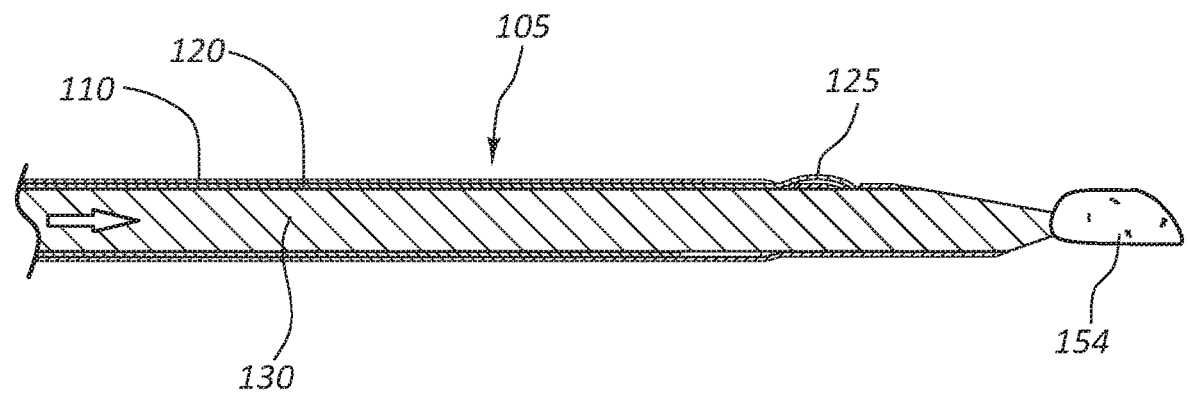
FIG. 8D is a schematic cross-sectional representation of the portions of the outer tubular member, the cutting member, and the trocar of the biopsy needle assembly of FIGS. 1A and 1B in a fourth configuration.

FIG. 8D illustrates the outer tubular member 110, the cutting member 120, and the trocar 130 of the needle assembly 105 in the fourth configuration. FIG. 8D depicts extraction of the tissue sample 154 from the biopsy needle assembly 105 following retraction of the biopsy needle assembly 105 and tissue sample 154 from the body tissue 150 of the patient. The cutting member 120 is displaced proximally relative to the outer tubular member 110 such that the tab 124 is displaced from the lumen 113 of the outer tubular member 110 permitting the tissue sample 154 to be displaced distally. The trocar 130 is displaced distally relative to the outer tubular member 110 and the cutting member 120 such that the trocar 130 displaces the tissue sample 154 from the lumen 113 of the outer tubular member 110. The extracted tissue sample 154 is displaced from the lumen 113 of the outer tubular member 110 such that the tissue sample 154 is a continuous sample of uniform diameter.

Without further elaboration, it is believed that one skilled in the art may use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art, and having the benefit of this disclosure, that changes may be made to the details of the above-described embodiments without departing from the underlying principles of the disclosure herein.

The invention claimed is:

1. A biopsy needle assembly configured for use with a tissue biopsy device, the biopsy needle assembly comprising:
   an outer tubular member comprising a distal end portion configured to sever a first portion of a tissue sample; and
   a cutting member slidably disposed within the outer tubular member, wherein the cutting member comprises a distal end portion, and wherein the distal end portion of the cutting member is configured to displace toward a central axis of the outer tubular member to sever a second portion of the tissue sample;
   wherein the distal end portion is configured to extend through an opening in the outer tubular member, the opening extending between an outside surface of the outer tubular member and a lumen of the outer tubular member.

2. The biopsy needle assembly of claim 1, wherein the distal end portion of the cutting member further comprises a tab, and wherein displacement of a portion of the tab into the lumen of the outer tubular member is configured to sever the second portion of the tissue sample.

3. The biopsy needle assembly of claim 2, wherein the at least one opening is configured to direct the portion of the tab into the lumen of the outer tubular member in response to relative displacement of the cutting member in relation to the outer tubular member.

4. The biopsy needle assembly of claim 3, wherein the portion of the tab is bent such that the tab is configured to enter the lumen of the outer tubular member through the opening.

5. The biopsy needle assembly of claim 2, wherein the tab is configured to sever the second portion of the tissue sample at or adjacent a distal-most point of the distal end portion of the outer tubular member.

6. The biopsy needle assembly of claim 1 wherein the cutting member is configured to sever the second portion of the tissue sample at an optimized position from a distal-most point of the distal end portion of the outer tubular member.

7. The biopsy needle assembly of claim 1, further comprising a trocar disposed within the cutting member, wherein the trocar comprises a distal end portion configured to facilitate advancement of the biopsy needle assembly through a body tissue.

8. A tissue biopsy device configured to obtain a tissue sample, comprising:
   a first elongate member configured to be advanced into a body tissue;
   a second elongate member movably disposed around the first elongate member and configured to sever a first portion of the tissue sample;
   a third elongate member movably disposed within the second elongate member and configured to sever a second portion of the tissue sample at or adjacent a distal-most point of a distal end portion of the second elongate member; and
   an actuator configured to actuate at least the second elongate member and the third elongate member such that the tissue sample is severed
   wherein a distal end portion of the third elongate member is partially disposed in an opening extending through a wall of the second elongate member prior to actuation, such that the distal end portion does not catch on tissue as the tissue biopsy device is advanced through tissue.

9. The device of claim 8, wherein the distal end portion of the third elongate member is configured to be displaced toward a central axis of the second elongate member to sever the second portion of the tissue sample.

10. The device of claim 9, wherein the distal end portion of the second elongate member is configured to direct the displacement of the distal end portion of the third elongate member.

11. The device of claim 8, wherein the third elongate member is further configured to extract the severed tissue sample from the body tissue.

* * * * *